United States Patent
Thorne et al.

(10) Patent No.: US 7,622,562 B2
(45) Date of Patent: *Nov. 24, 2009

(54) RAPID ISOLATION OF OSTEOINDUCTIVE PROTEIN MIXTURES FROM MAMMALIAN BONE TISSUE

(75) Inventors: Kevin Thorne, Austin, TX (US); Rama Akella, Austin, TX (US)

(73) Assignee: Zimmer Orthobiologics, Inc., Austin, TX (US)

(*) Notice: Subject to any disclaimer, the term of this patent is extended or adjusted under 35 U.S.C. 154(b) by 394 days.

This patent is subject to a terminal disclaimer.

(21) Appl. No.: 11/553,640

(22) Filed: Oct. 27, 2006

(65) Prior Publication Data

US 2007/0049731 A1 Mar. 1, 2007

Related U.S. Application Data

(63) Continuation-in-part of application No. 10/606,190, filed on Jun. 25, 2003, now Pat. No. 7,241,874.

(60) Provisional application No. 60/391,566, filed on Jun. 26, 2002.

(51) Int. Cl.
  *C07K 14/51* (2006.01)
  *C07K 14/435* (2006.01)
  *C07K 1/14* (2006.01)
  *C07K 1/34* (2006.01)
  *A61K 35/32* (2006.01)

(52) U.S. Cl. .................. 530/840; 530/412; 514/21; 424/549

(58) Field of Classification Search .................. None
See application file for complete search history.

(56) References Cited

U.S. PATENT DOCUMENTS

| | | | |
|---|---|---|---|
| 4,172,128 A | 10/1979 | Thiele et al. | 424/95 |
| 4,294,753 A | 10/1981 | Urist | 260/112 R |
| 4,455,256 A | 6/1984 | Urist | 260/112 R |
| 4,596,574 A | 6/1986 | Urist | 623/16 |
| 4,619,989 A | 10/1986 | Urist | 530/417 |
| 4,743,259 A | 5/1988 | Bolander et al. | 623/16 |
| 4,874,746 A | 10/1989 | Antoniades et al. | 514/21 |
| 4,902,296 A | 2/1990 | Bolander et al. | 623/16 |
| 5,236,456 A | 8/1993 | O'Leary et al. | 623/16 |
| 5,256,644 A | 10/1993 | Antoniades et al. | 514/12 |
| 5,290,558 A | 3/1994 | O'Leary et al. | 424/422 |
| 5,290,763 A | 3/1994 | Poser et al. | 514/21 |
| 5,371,191 A | 12/1994 | Poser et al. | 530/350 |
| 5,393,739 A | 2/1995 | Bentz et al. | 514/12 |
| 5,484,601 A | 1/1996 | O'Leary et al. | 424/422 |
| 5,516,532 A | 5/1996 | Atala et al. | 424/548 |
| 5,563,124 A | 10/1996 | Damien et al. | 514/21 |
| 5,830,859 A | 11/1998 | Schmidt | 514/12 |
| 5,968,556 A | 10/1999 | Atala et al. | 424/548 |
| 6,118,043 A | 9/2000 | Nies et al. | 623/16 |
| 6,120,760 A | 9/2000 | Hötten et al. | 424/85.1 |
| 6,180,605 B1 | 1/2001 | Chen et al. | 514/12 |
| 6,305,379 B1 | 10/2001 | Wolfinbarger, Jr. | 128/898 |
| 6,511,958 B1 | 1/2003 | Atkinson et al. | 514/2 |
| 6,514,514 B1 | 2/2003 | Atkinson et al. | 424/423 |
| 6,534,095 B1 | 3/2003 | Moore-Smith et al. | 424/549 |
| 6,627,230 B2 | 9/2003 | Benedict et al. | 424/549 |
| 7,341,999 B2 | 3/2008 | Akella et al. | 514/21 |
| 2001/0007023 A1 | 7/2001 | Lough, Jr. et al. | 530/841 |
| 2001/0041792 A1 | 11/2001 | Donda et al. | 530/399 |
| 2002/0173453 A1 | 11/2002 | Akella et al. | 514/12 |
| 2003/0176345 A1 | 9/2003 | Dawson | 514/12 |
| 2004/0072322 A1 | 4/2004 | Thorne | 435/226 |
| 2005/0064041 A1 | 3/2005 | O'Leary et al. | 424/549 |
| 2005/0096274 A1 | 5/2005 | Lough et al. | 514/12 |
| 2006/0057184 A1 | 3/2006 | Nycz et al. | 424/426 |
| 2006/0286157 A1 | 12/2006 | Akella et al. | 424/445 |
| 2007/0066525 A1 | 3/2007 | Lee et al. | 514/12 |

FOREIGN PATENT DOCUMENTS

| | | |
|---|---|---|
| EP | 0 243 179 B1 | 10/1992 |
| WO | WO88/03409 | 5/1988 |
| WO | WO 92/18142 | 10/1992 |
| WO | WO01/66130 | 9/2001 |
| WO | WO02/00244 | 1/2002 |
| WO | WO02/47713 | 6/2002 |
| WO | WO2005/084701 | 9/2005 |
| WO | WO2006/093545 | 9/2006 |
| WO | WO2007/053850 | 5/2007 |

*Primary Examiner*—Vera Afremova
(74) *Attorney, Agent, or Firm*—Howrey LLP

(57) ABSTRACT

A method for purifying bone-derived osteoinductive proteins including a demineralization process, a protein extraction process, a high molecular weight ultrafiltration process, a low molecular weight ultrafiltration process, and a recovery process. The high and low ultrafiltration processes preferably select proteins having a nominal molecular weight between approximately 8 kilodaltons and approximately 100 kilodaltons. Processes of the present invention may be used to recover osteoinductive proteins from bone demineralization waste streams.

16 Claims, No Drawings

RAPID ISOLATION OF OSTEOINDUCTIVE PROTEIN MIXTURES FROM MAMMALIAN BONE TISSUE

CROSS-REFERENCE TO RELATED APPLICATIONS

This application is a continuation-in-part of U.S. patent application Ser. No. 10/606,190, filed Jun. 25, 2003, now U.S. Pat. No. 7,241,874 which claims priority to U.S. patent application Ser. No. 60/391,566, filed Jun. 26, 2002, the disclosures of which are hereby incorporated herein by reference.

FIELD OF THE INVENTION

The present invention relates generally to methods for the rapid, high yield recovery and isolation of bone morphogenetic proteins (BMPs) and other tissue-inductive proteins from mammalian bone. In another aspect, the invention relates to protein mixtures recovered from bone demineralization waste streams. The invention also comprises protein mixtures produced according to the foregoing methods, and to implantable devices for osteoinductive repair of bone and tendon repair or reconstruction.

BACKGROUND OF THE INVENTION

Mammalian bone tissue comprises a number of proteins, including structural proteins such as collagen as well as osteoinductive proteins that induce or promote bone growth. Recognition of the existence of osteoinductive proteins in bone tissue has led to the discovery of a family of protein molecules known as the Bone Morphogenetic Proteins (BMPs). BMPs are members of the TGF β superfamily of proteins, which includes additional proteins that provide tissue-inductive responses in vivo, including TGF-β1, TGF-β2, and TGF-β3. Structures for proteins designated BMP-1 through BMP-18 have been isolated and additional related proteins found. Additional information regarding the BMPs can be found in U.S. Pat. Nos. 6,511,958 and 6,514,514, which are hereby incorporated by reference. The unique inductive activity of the BMPs, along with their presence in bone tissue, suggests they are involved in the regulation of bone repair processes and possibly in the normal maintenance of healthy bone tissue. There is a great need for such proteins for the induction and/or augmentation of bone growth following surgical bone repair or reconstruction procedures in human and animal patients.

Much research has been directed to producing, either by recombinant DNA techniques or by purification of naturally occurring proteins, specific osteoinductive proteins and protein mixtures. Protein mixtures having BMPs and other inductive proteins may be isolated from bone tissue according to known procedures. One of the earliest such procedures is disclosed in U.S. Pat. No. 4,294,753 to Urist, which provides a process for isolating bone proteins from bone tissue by demineralizing the bone tissue in acid. The demineralized collagen bone matrix is reduced to gelatin by adding a mineral salt. Osteoinductive BMPs are extracted from the gelatin using a solubilizing agent, such as guanidine hydrochloride and/or urea. The solubilized proteins are then purified by dialysis and several washing steps.

The processes disclosed in the '753 patent are also inherently inefficient. The demineralization step—the first step in the BMP isolation procedure—involves contacting the bone with hydrochloric acid to dissolve the mineral components of the bone and separate them from the protein components. The mineralized acid medium is discarded. Because BMPs are soluble in acids, a significant fraction of the BMPs can be lost from the beginning of processing.

The chemical reagents used to solubilize and extract the osteoinductive proteins from the demineralized bone in the '753 procedures, i.e., guanidine hydrochloride (GuHCl) and urea, are cytotoxic. Consequently, the bone proteins must be subjected to extensive and time-consuming purification procedures to ensure that the BMPs obtained by the isolation procedures are free of cytotoxic agents and remain osteoinductive when administered to the patient.

U.S. Pat. No. 4,619,989, also to Urist, discloses an improved process for isolating BMPs that involves additional dialysis purification steps beyond those disclosed in the '753 patent. Such steps increase still further the time required to isolate usable BMP mixtures. In addition, the additional purification steps further reduce protein yield and, worse still, may remove BMP fractions that are either osteoinductive per se or have a synergistic effect with the remaining BMP proteins.

An improved method of isolating and purifying BMP-containing mixtures is described in U.S. Pat. Nos. 5,290,763 and 5,371,191. Both the '763 and '191 patents disclose a multistep process to provide highly purified BMP-containing mixtures. The process involves demineralization, protein extraction, high and low molecular weight ultrafiltration steps, an anion exchange process, a cation exchange process, and a reverse-phase HPLC process. Although the resulting BMP-containing mixture is highly osteoinductive, the process is lengthy, requires expensive equipment, and has low yields.

There remains a need for BMP mixtures that may be easily, quickly and economically isolated from bone tissue in high yields, promote rapid osteoinduction when implanted in a human or animal patient, and that are amenable to combination with a wide variety of carriers.

It is an object of the present invention to provide a rapid, efficient, and economical process for obtaining osteoinductive BMP mixtures from mammalian bone tissue.

It is another object of the present invention to provide processes for recovering osteoinductive BMPs from bone demineralization waste streams.

It is another object of the invention to provide a process for obtaining osteoinductive BMP mixtures in high yields from mammalian bone tissue.

It is a still further object of the invention to provide a method of isolating osteoinductive BMP mixtures from mammalian bone tissue that minimizes loss of BMPs from the bone tissue source.

It is a further object of the invention to provide a method of isolating osteoinductive BMP mixtures from mammalian bone tissue that minimizes or avoids altogether the use of time-consuming dialysis procedures.

It is a further object of the invention to provide protein mixtures prepared by the foregoing processes.

It is a further object of the invention to provide compositions and/or implantable devices comprising a mixture of BMPs isolated from mammalian bone tissue.

SUMMARY OF THE INVENTION

In one embodiment, the present invention comprises an improved and simplified process for the rapid, high yield recovery and isolation of osteoinductive BMPs from mammalian bone. In particular, the method comprises providing clean bone particles, demineralizing the particles in a demineralization medium to provide demineralized bone matrix (DBM) particles, extracting BMPs from the DBM particles with an extracting agent, removing undesired high and low molecular weight compounds, and purifying the BMPs to obtain the BMP mixtures either in a solvent or in a solid form.

It is believed that about 75% of the osteoinductive proteins in bone tissue remain bound to the bone collagen during bone demineralization, and may subsequently be recovered by conventional extraction processes known in the art. The 25% of inductive proteins that are lost due to acid solubilization during bone demineralization constitutes a significant loss of osteoinductive proteins and activity. Accordingly, in one aspect, the invention provides a method to additionally recover and isolate the BMPs from this acid waste fraction.

Demineralization yields an acidic solution of solubilized bone mineral and osteoinductive bone matrix proteins, and insoluble demineralized bone powder. Because of fundamental differences in solution and matrix chemistry, separate processing protocols are described to facilitate extraction and recovery of osteoinductive proteins from the soluble and insoluble components of the demineralization process.

In a preferred embodiment, clean bone particles or fragments are demineralized with a suitable acid, preferably hydrochloric acid, at a low pH (less than about 3.5). Hydrochloric acid is both highly acidic and can be substantially completely eliminated from a product by gaseous evolution during lyophilization. Some BMPs may be extracted from the bone tissue by the demineralizing solution. Accordingly, the acid supernatant comprising the extracted mineral components of the bone tissue also comprises BMPs and, in one embodiment of the invention, is further treated to recover osteoinductive proteins therefrom. However, a separate protein extraction agent is also preferably employed to better extract the proteins from the demineralized bone particles after separation from the mineralized supernatant. In particular, BMPs are preferably extracted from the DBM particles using guanidine hydrochloride (GuHCl), although urea or other chaotropes or mixtures thereof may also be used as a protein extraction agent.

The GuHCl extract solution is filtered or centrifuged to remove large particles, and preferably subjected to two ultrafiltration steps, preferably tangential flow filtration (TFF). In the first ultrafiltration step, high molecular weight compounds are removed in a High Molecular Weight Ultrafiltration (HMWU) step. An ultrafiltration membrane having a nominal molecular weight cut off (MWCO) of 100 kD is preferably employed, although other nominal MWCO membranes (e.g., 60, 70, 80, 90, 110, or 120 kD) may alternatively be used.

The retentate (larger particles) is discarded and the filtrate is subjected to a second ultrafiltration step to remove low molecular weight compounds in a Low Molecular Weight Ultrafiltration (LMWU) step. An ultrafiltration membrane preferably having a nominal MWCO of about 8 kD is preferred, although larger or smaller nominal MWCO membranes (e.g., 5 kD, 7 kD, 10 kD, 12 kD, or 15 kD) may be used.

The desired osteoinductive BMPs are separated from the protein extraction agent by one or more filtration steps, preferably one or more diafiltration steps. Because removal of GuHCl is especially important, the BMPs are diafiltered into low concentration GuHCl solution. To remove the remaining chaotrope, the final purification of the BMP mixtures is preferably performed by one or more purification steps such as lyophilization or precipitation. The purified BMP mixture may be redissolved in a suitable carrier liquid, such as 10 mmol HCl, or may be recovered in solid form, e.g., lyophilization, before packaging.

In another embodiment, the invention comprises a method for purifying BMP from bone tissue comprising demineralizing bone particles by contacting the bone particles with an acidic demineralization medium, extracting BMPs from the demineralized bone particles with an extracting agent, removing compounds having a molecular weight greater than a desired upper molecular weight threshold (e.g., 100 kD) by a high molecular weight filtration step, removing compounds having a molecular weight below a desired lower molecular weight threshold (e.g., 8 kD) by a low molecular weight filtration step, and recovering BMPs from the filters. Optionally, additional purification steps such as lyophilization, resuspension and/or precipitation may be performed.

In another aspect, the present invention comprises methods for recovery of osteoinductive BMPs from a bone demineralization waste stream. More particularly, the present invention comprises contacting bone particles with an acidic demineralization medium, separating the mineralized supernatant solution from the demineralized bone particles, optionally removing at least a portion of the minerals from the mineralized supernatant solution to provide a protein supernatant solution, extracting BMPs by contacting the protein supernatant solution with a protein extraction agent, removing undesired high and low molecular weight compounds, purifying the BMPs, and recovering the BMPs either in a liquid solvent or in a solid form.

In a further embodiment, the invention comprises methods for recovering osteoinductive BMPs from a bone demineralization medium. One such method comprises demineralizing bone particles in an acid medium, separating the demineralized bone particles from the mineral-containing acid supernatant, and recovering BMPs from the mineralized acid supernatant. The mineral-containing acid supernatant may be treated with a mineral precipitation agent to remove at least a portion of the mineral from the supernatant, providing a protein supernatant solution. The BMPs may be extracted from the protein supernatant with a protein extraction agent, and recovered from the extracted protein medium by removing undesired high and low molecular weight compounds, purifying the BMPs, and recovering the BMPs either in a liquid solvent or in a solid form.

In another embodiment, the invention comprises an osteogenic implant device for promoting or augmenting bone growth. The device comprises BMP mixtures obtained by the rapid purification methods described herein and an acidic matrix. In one embodiment, the acidic matrix comprises collagen and an acidic calcium phosphate salt.

DETAILED DESCRIPTION OF THE INVENTION

In one embodiment of the present invention, the process for producing BMP mixtures comprises providing clean bone tissue particles, demineralizing the particles, extracting BMPs from the particles, removing high and low molecular weight components by ultrafiltration, and purifying the BMP mixture by diafiltration, lyophilization and/or precipitation.

The starting material for the present process is mammalian bone, including human bone. Non-human animal bone, examples of which include but are not limited to bovine, ovine, equine, or porcine bone, may also be used, however, because it is readily available at low cost. Bovine bone is preferred. Cortical bone tissue is preferred, although cancellous bone or corticocancellous bone can also be used. Human cortical bone tissue obtained from bone banks has been cleaned and ground according to established protocols, from a documented source, and may be obtained in particle size distributions that are amenable to BMP extraction. A preferred size distribution for the particles is about 1000 μm or less.

Alternatively, starting bone tissue may be obtained from mammalian bone obtained from, e.g., an abbatoir, by cleaning operations known in the art, such as removing all soft tissue and then grinding and further cleaning the bone. High-pressure washing is preferably employed to clean the bone tissue prior to grinding, and its use may minimize—and preferably eliminate altogether—subsequent soaking and flotation steps, as described by U.S. Pat. No. 6,627,230, to Benedict et al., incorporated herein by reference. U.S. Pat. No. 5,371,191 to Poser et al., which is hereby incorporated by reference herein in its entirety, discloses other cleaning methods for bovine bones suitable for use in the present invention. Typically, the bone is ground into successively finer particles and soaked in detergent solution to remove non-bone material. The bone is ground to particles less than 4 mm in size, preferably about 1000 μm or less. The ground bone particles are soaked in detergent solution between grindings, and rinsed in a flotation tank to remove soft tissue.

In one embodiment, soft tissue (e.g., marrow, periosteum, fat, blood, and other material) is removed from corticocancellous bone and the corticocancellous bone is pulverized to particles having a size range of about 100 μm to about 1000 μm, such as about 200 μm to about 800 μm. The particles are defatted by soaking in stirred deionized water for at least about 3 hr at about 37° C.

In a preferred embodiment, cleaned bone tissue is demineralized by soaking the particles in a suitable acid to dissolve its mineral content. Hydrochloric acid is preferred, although other acids such as formic acid, among others, can alternatively be used. A solution of dilute HCl, preferably in a range of from about 0.6N to about 4.0N, more preferably from about 1.0N to about 3.0N, most preferably 2.0 N, is effective to demineralize bone. It is preferred that the pH of the demineralizing solution be controlled during demineralization at from about 0.4 to about 5.0, preferably from about 0.4 to about 2.0, more preferably at about 1.5 to prevent collagen hydrolysis.

The bone minerals and proteins are less soluble in lower acid concentrations (i.e., higher pH. Accordingly, it is theorized that low acid concentrations (or higher pH) should correspond to higher solution volumes, lower viscosity in the mixture, and higher filtration rates for the filtration steps in the process. On the other hand, the lower solubility of the proteins in lower acid concentrations also should result in higher protein loss during filtration, associated with the adhesion of proteins to the filtration membranes. Higher acid concentrations (lower pH), conversely, should result in faster mineral solubilization and smaller working solution volumes, but higher viscosity and thus slower filtration rates.

The demineralization solution may be agitated with, e.g., a stirrer, and is preferably maintained at room temperature. Additives such as $CaCl_2$ or other salts or organic solvents in which minerals are soluble, such as ethylenediamine tetraacetic acid (EDTA), can be used to enhance the solubility of the bone minerals if desired. Salts such as $CaCl_2$ are generally more effective at enhancing the solubility of the bone materials. Octyl alcohol or other defoaming agents (such as hydrocarbons such as mineral oils, white oils, or paraffins; alcohols; fatty acids; fatty acid salts of multivalent cations; esters, including fats, waxes, and phosphoric esters; amides, including amide waxes; silicone oils; and silicas) may also be used to prevent excessive foaming during demineralization. Alcohols are generally simpler to use and more effective than other materials.

The bone is soaked in acid until the bone is essentially fully demineralized. X-ray analysis may be used to evaluate the extent of demineralization. Alternatively, standard procedures can be developed through experience to determine the amount of time required for demineralization. Typically, at least two hours is required, although additional time may be required for larger batches.

In one embodiment, defatted corticocancellous bone particles are demineralized by contact with 2N HCl (pH ~0.6) with stirring for at least about 3 hr at a temperature from about room temperature to about 37° C., wherein the pH of the slurry containing bone particles and HCl is kept at about pH 1.5 or less, such as from about pH 1.5 to about pH 0.6. The slurry is centrifuged, for example, at about 4000 rpm for about 12 min to about 15 min at room temperature, to yield a demineralized bone (DMB) pellet and an acid supernatant containing minerals, which may also be termed an acidic demineralization solution.

Prior art approaches, e.g., as described in U.S. Pat. Nos. 4,294,753 and 4,455,256, both of which are hereby incorporated by reference in their entirety, describe discarding the acidic demineralization solution by dialysis and washing steps. Similarly, the approach described in U.S. Pat. No. 5,371,191 also discloses discarding the HCl demineralization solution. It is believed that the high solubility of BMPs in acid results in extensive and unnecessary loss of osteoinductive proteins in prior art BMP isolation processes. Accordingly, in contrast to prior art approaches, the present invention contemplates recovery of BMPs from the mineral-containing HCl demineralization solution.

BMP recovery from the acidic demineralization solution may be accomplished by adding a protein extraction agent directly to the HCl-and-bone-tissue acidic demineralization solution, by separating the mineralized acid supernatant from the demineralized bone particles, removing at least a portion of the minerals (primarily calcium phosphate) from the mineralized supernatant solution, and adding a protein extraction agent to the supernatant to extract the BMPs and yield an extracted protein medium, or by tangential flow filtration alone. The extracted protein medium may then be purified by the same procedures as outlined herein for the extract medium for the DBM particles. Alternatively, the extracted protein medium may be combined with the extraction medium from the DBM particles at some point in the processing procedures, and all of the BMPs from the bone tissue may be recovered as a single stream.

In one embodiment, BMPs are extracted from the DMB particles (and/or solubilized in the HCl demineralization supernatant) by adding a suitable extraction agent, preferably high purity GuHCl, although urea or other extraction agents may be alternatively used. GuHCl is a preferred denaturant because it is ionic and therefore also functions well as a solubilizing agent for maintaining proteins in solution. Where GuHCl is employed, concentrations may range from 1M to 8M or to the solubility limits of the GuHCl. Preferred concentrations are from 2M to 8M, more preferably 4M. Lower concentrations allow less expensive extraction, as less GuHCl is used, but with slower solubilization of the BMPs and possibly lower bioactivity and/or yields.

Preferably the GuHCl extraction is performed at about body temperature (37° C.), although lower temperatures may also be used. The temperature of the denaturant can increase during the extraction process. A 4M GuHCl, pH 7.0 solution is a preferred extraction solution. Optionally, a chaotrope can be added during extraction to improve solubility of extracted proteins. Suitable chaotropes include calcium chloride ($CaCl_2$), magnesium chloride ($MgCl_2$), and cesium chloride (CsCl$_2$). Usually, extraction continues until substantially all of the noncollagenous bone proteins have been removed from the demineralized bone. A typical extraction takes about 3 hours, although higher yields can be obtained by increasing the extraction time (such as up to about 72 hr).

In one embodiment, the DMB pellet is subjected to a water wash to collect at least part of a water-soluble BMP fraction. The water wash can then be added to the demineralized acidic supernatant for further processing or it can be processed separately. The DMB pellet is then washed with PBS (phosphate buffered saline), such as 20× concentration PBS neutralized to about pH 6.5 with agitation, and the DMB and PBS wash are centrifuged, such as at 4000 rpm for about 12 min to about 15 min at room temperature. The DMB pellet is retained and the PBS wash is discarded. Multiple PBS washes can be performed, but one is frequently sufficient. The DMB pellet is then washed with deionized water to remove residual PBS salts and the DMB pellet is separated by centrifugation, as described above. Multiple deionized water washes, such as about three, can be performed. After the deionized water wash(es), the DMB pellet is solubilized with Tris/GuHCl, pH about 6.8 to about 7.0, with shaking for a relatively long duration, such as about 72 hr. The Tris/GuHCl-DMB slurry is then centrifuged and the GuHCl supernatant, which contains BMPs, is retained and subjected to TFF with a 100 kDa MWCO and the permeate (which contains BMPs) is collected. The permeate is subjected to TFF with an 8 kDa MWCO and the retentate (which contains BMPs) is collected. GuHCl is substantially eliminated from the retentate by diafiltration, lyophilization, and about three or four cycles of ethanol precipitation. The final precipitate, containing BMPs, can then by lyophilized and solubilized in 10 mM HCl for storage.

Following demineralization, BMPs and other osteoinductive proteins in the demineralized bone extract solution are then separated by two ultrafiltration steps to remove proteins larger than a high molecular weight limit, preferably 100 kD, and smaller than a low molecular weight limit, preferably 8 kD. The filtration is preferably tangential flow filtration (TFF). TFF provides a rapid and efficient method for concentrating dissolved molecules, (i.e., proteins, peptides, nucleic acids, carbohydrates and other biomolecules), desalting or exchanging solution buffers and gross separation/fractionation. TFF is routinely used on solution volumes ranging from 200 ml to hundreds of liters and is capable of concentration them to volumes as small as 10 ml in a short period of time. TFF allows much faster and more convenient concentration, desalting, and fractionation than conventional dialysis, the process uses membrane filter cassettes that can be used more than once and the process can be easily scaled. Simple control of materials, membrane surface area and filtration path length allow for direct translation of conditions established during pilot scale to process or commercial scale.

TFF flow filtration can be used to eliminate soluble bone mineral components from the waste demineralization acid wash because of their extremely small size. To facilitate the effective and simultaneous recovery of a desired molecular weight range of proteins, a chaotrope or denaturing agent may be added to denature and deagglomerate the proteins. The use of a chaotrope or denaturing agent is optional. Guanidine hydrochloride is an example of a highly effective denaturing agent, but it functions effectively only at neutral pH (~7) values. Buffering the acidic waste stream to a neutral pH will stimulate the (re)precipitation of calcium phosphate mineral residues from the acid wash. Although a fraction of osteoinductive proteins may remain in solution, a fraction may be eliminated from solution during mineral precipitation because of the osteoinductive proteins' affinity for hydroxyapatite. An active protein residue can be recovered via this process. TFF filtration of the direct mineral waste solution can also allow soluble salt reduction.

Returning to the ultrafiltration steps, the extract solution is preferably first subjected to a high molecular weight ultrafiltration step in which proteins larger than the high molecular weight limit are removed. The high molecular weight ultrafiltration step advantageously separates soluble osteoinductive BMPs from high molecular weight collagens, and although the entire procedure is preferably conducted with sterile bone, instruments and reagents, the HMWU also eliminates any extraneous bacteria and other microorganisms to ensure a sterile product. Ultrafiltration steps having pore sizes smaller than most bacteria, e.g., 20 microns or less permit sterilization by filtration.

In a preferred embodiment, the HWMU step is performed in a Millipore Pellicon® Model tangential flow filtration (TFF) apparatus using a 100 kD nominal MWCO, polyether sulfone (PES) filter to minimize protein adhesion to the filter material. It is preferred to select a filter with relative low protein binding to the filter material itself The ultrafiltration is preferably conducted at temperatures in the range of 2° C. to 50° C., preferably about 4° C. Other MWCO filters could be used, from about 50 kD to about 120 kD or even higher, as the HWMU step MWCO filter. A TFF apparatus is preferred because such systems are readily scalable to larger (i.e., commercial) batch sizes. The retentate (i.e., material having a MW greater than the nominal MWCO of the filtration apparatus) from the HMWU step is discarded.

The HMWU permeate is then subjected to a LMWU step in which proteins smaller than a low molecular weight limit are removed. The LWMU step is preferably performed in a TFF apparatus using an 8 kD nominal MWCO, PES filter, or other filter having low protein binding. Because of the small pore size of the filters in the LWMU step, it may be desirable to dialyze the filters or wash with HCl or another acid to assist in the passage of GuHCl through the filter.

Although an 8 kD MWCO filter is preferred, larger or smaller nominal MWCO filters could be used, ranging from 5 kD to 15 kD, as the LMWU step MWCO filter. The ultrafiltration is preferably conducted at 4° C., although temperatures ranging from 2° C. to 50° C. (or even higher, so long as the proteins are not completely denatured or permanently inactivated) are permissible. The LWMU step yields a retentate with a mixture of proteins having molecular weights within a desired range.

The retentate from the LWMU step comprises a mixture of BMPs and other osteoinductive and non-osteoinductive proteins that may be implanted in a human or animal patient to promote bone growth. It is essential that the extraction agent be removed from the BMPs. GuHCl is removed by a diafiltration in a TFF apparatus into GuHCl at about 1.0M. The proteins are then recovered by lyophilization, followed by precipitation with ethanol, resuspension in HCl and lyophilization. Additional purification by washing and/or reprecipitation of the BMPs from the wash medium may be provided.

The BMPs may advantageously be stored in sterile containers either as an osteoinductive solution or as a lyophilized solid. It is preferred to maintain the solution or solid either under vacuum or inert gas atmosphere such as e.g., nitrogen, hydrogen, helium, argon, or mixtures thereof.

Where the BMPs are maintained in an osteoinductive solution, the proteins may be used by adding the solution to a solid carrier such as collagen or bone chips, or by mixing the solution with a liquid or slurried carrier such as saline, blood, plasma, serum, PRP, or bone marrow aspirate.

Where the BMPs are maintained as a lyophilized solid, the proteins may be combined with another solid carrier, such as collagen, hydroxyapatite, or a composite device.

In one embodiment, the acidic demineralization supernatant derived from the demineralization step (and, optionally, supplemented with a water wash from the DMB pellet) is subjected to TFF with a 100 kDa MWCO and the permeate (which contains BMPs) is collected. The permeate is subjected to TFF with an 8 kDa MWCO and the retentate (which contains BMPs) is collected. The retentate can be used to backwash the TFF membrane. The retentate is lyophilized, which will evaporate HCl from the retentate. Proteins, particularly including BMPs, are then precipitated from the lyophilized retentate by the use of ethanol. The precipitated proteins can then be lyophilized and resuspended in 10 mM HCl for storage. The steps of this embodiment can be performed without the addition of GuHCl or other denaturing agents and also without the addition of chaotropes.

Useful features of the present invention include the extraction of osteoinductive proteins from acid solution, as opposed to the discarding of the acid solution as reported in the art. This extraction involves the substantial separation of minerals via precipitation prior to protein extraction, as opposed to contemporaneous dialysis. The demineralized acid solution can be combined with DMB or DBM for joint protein extraction or protein extractions on the demineralized acid solution and the DMB or DBM prior to combination. The present invention can also involve the combining of osteoinductive proteins from water washes with osteoinductive proteins extracted from demineralized acid solution.

EXPERIMENTAL

Experiment 1

Demineralization of Bone Tissue

The following experimental protocol is one embodiment of the invention for isolating BMP mixtures. It has been used to isolate BMPs from human bone tissue that exhibit osteoinductive activity in rats. Other mammalian sources, preferably bovine or porcine, may also be used. All operations are conducted aseptically with sterile reagents and sterile equipment. A batch size of 100 g starting mineralized bone tissue has been used, but in commercial operation the batch size would preferably be much larger.

One hundred grams of clean, sterile mineralized human bone particles of 1000 microns or less was obtained from a certified bone bank source. The mineralized human bone powder was defatted with water heated to 37° C. In a sterile container with continuous agitation, approximately 500 ml of sterile water was added to the bone powder. The solution was warmed to 37° C. for one hour, after which the bone powder was separated from the water by centrifugation (3000 rpm for 15 minutes). The procedure was repeated twice to ensure complete lipid removal. Other lipid removal techniques known in the art may also be used, including the use of organic solvents such as alcohol, acetone, or the like. Removing lipids from the bone powder facilitates rapid and complete isolation of BMPs.

Following the defatting procedure, the bone powder was demineralized. In a sterile container with continuous magnetic stirring, approximately 500 ml of sterile 2 N HCl was added to the bone powder until the pH stabilized at 1.5. Higher concentrations of HCl (e.g., 3.0M to 5.0M) may be used but are more likely to fragment collagen molecules in the bone tissue, thus increasing viscosity and filtration time. The demineralization was allowed to proceed for about three hours after stabilization of the pH.

As the initial HCl was added, the mineral content of the bone was solubilized, increasing the pH. Initially, the pH rose rapidly, requiring frequent addition of HCl (each minute or even more frequently for the first several minutes) during the first thirty minutes of the procedure. After about thirty minutes, the pH stabilized at 1.5 and further addition of acid was not required. Demineralization may take from 1-24 hours, more preferably from 2-10 hours, and even more preferably from about 3 to about 3½ hours.

When the demineralization was complete, the acid was separated from the bone collagen by centrifugation at 3000 rpm for 20 minutes. Other separation methods known in the art may also be used, however. The supernatant was decanted for further processing, as described more fully in Experiment 6 below. After demineralization, the remaining tissue comprises primarily demineralized bone collagen containing osteoinductive proteins, and is known as demineralized bone (DMB). The DMB was washed with successive sterile water and/or phosphate buffered saline (PBS) rinses until the pH reached 7.0, indicating complete acid removal.

Each wash was conducted by suspending the DMB in about 250 ml of water or PBS per 100 g starting mineralized bone, stirring for about 20 minutes at room temperature, and then separating the wash and DMB, preferably by centrifugation as described previously. The wash solution (i.e., water or PBS) was decanted after each wash. Some osteoinductive proteins may be present in the wash supernatant, and the initial water washes may be saved and combined with the original acid supernatant from the demineralization step for later BMP recovery according to the protocol in Experiment 6 below. The number of water washes saved will depend on the anticipated or measured BMP concentration thereof. However, under the conditions described in this experiment, typically only the first water wash supernatant is saved.

Three water washings were performed on the DMB. The bone was also further rinsed once overnight with 20× concentration PBS (i.e., phosphate buffered saline having twenty times the standard phosphate buffer concentration) with magnetic stirring to raise the pH to 7.0. After rinsing with 20× PBS, the DMB was further subjected to three sterilized water rinses to remove the saline buffer. After rinsing was completed, the bone was frozen at −80 C for 1-2 hours, and then lyophilized overnight (or longer). After lyophilization, the mass of the DMB was measured. Demineralized bone is typically about 40% of the starting mass of the mineralized bone.

The bone powder was acid demineralized according to known procedures. The previously described procedure provides one acceptable protocol. However, persons of skill in the art will readily appreciate that alternate protocols may also be followed with similar, acceptable results. However, saving the acid demineralization supernatant and/or the water wash supernatant for BMP recovery are not known in the art.

Experiment 2

Extraction of BMPs from Demineralized Bone

After demineralization, the DMB was extracted with filter-sterilized guanidine hydrochloride (GuHCl) to solubilize the BMPs. In particular, 500 ml of 4.0M GuHCl, pH 7.0, was added to the DMB per 100 g starting mineralized bone. The extraction was continued for 72 hours with constant agitation in an incubator at 25° C. However, except for the extent they may deleteriously impact bone protein recovery and/or activity, extraction conditions are not critical and longer or shorter time periods and higher or lower temperatures can be used acceptably. A preferred range of extraction times is 24-96 hours. Lower temperatures, down to about 0° C. may be used so long as the reagents remain in the liquid state. Similarly, higher temperatures may be used, the upper limit being determined by the increased denaturation and/or activity loss of some of the osteoinductive proteins. For this reason, temperatures below 50° C. are preferred.

After the extraction was complete, the GuHCl and dissolved osteoinductive proteins were separated from the extracted DMB by centrifugation at 10,000 rpm for 10 minutes. The liquid supernatant was decanted for further processing. To ensure that all osteoinductive proteins were recovered, the extracted DMB was washed once with 100 ml of sterile water and centrifuged as before. The supernatant water and any additional osteoinductive proteins therein were added to the decanted GuHCl extract. Extracted DMB, essentially pure bone collagen that has been depleted of its osteoinductive proteins, is known as demineralized and devitalized bone matrix ("DVBM"). The DVBM was frozen and lyophilized as described for the demineralized bone. DVBM may be used as a matrix component for delivery of osteoinductive proteins.

Experiment 3

High and Low Molecular Weight Ultrafiltration

The GuHCl extract, optionally including the water from the rinse step, was then filtered in a HMWU step to remove high molecular weight, non-osteoinductive proteins such as collagen and large collagen fragments, preferably in a Millipore Pellicon XL TFF apparatus. The filters are preferably made of a material that does not bind proteins such as polyethersulfone (PES). A TFF apparatus with a 100 kD molecular weight cutoff (MWCO) filter was used to process the extract collected from Example 2, although other MWCO filters such as 60, 70, or 75 may be used. The GuHCl extract was circulated until the retentate was concentrated by a factor of from about two to about 100, i.e., the retentate volume ranges from one-half to one-hundredth of the volume added to the TFF apparatus. In the present Example, the retentate was concentrated about ten-fold, i.e., the retentate was concentrated to about one-tenth of the volume added to the TFF apparatus. Thus, for a starting volume of about 500 ml GuHCl extract, the retentate was concentrated to 50 ml.

The collected TFF permeate from the HMWU step, which contained the extracted proteins in GuHCl, was then passed through a low molecular weight TFF apparatus.

The desired proteins from the HMWU step permeate were separated from lower molecular weight compounds in a Low Molecular Weight Ultrafiltration (LMWU) step using a TFF apparatus with a filter having an 8 kD MWCO. Alternate embodiments are possible using different filter sizes, preferably in the range of from 2 kD-12 kD, more preferably 5-10 kD. It is preferred that the filter comprise non-protein-binding materials such as PES as already discussed. In contrast to the removal of high molecular weight compounds discussed above, in the removal of low molecular weight compounds the retentate, rather than the permeate, retains the desired proteins, which generally are in the range of 13-36 kD. Thus, low molecular weight compounds such as GuHCl pass through the 8 kD MWCO filter and the desired proteins are retained. In the present Example, the volume of the HMWU step permeate was about 1.8 liters. This volume was concentrated to about 50 ml. Thus, the low molecular weight TFF step may concentrate the GuHCl by a factor of from about two to about 1000, in the present Example about 36-fold. To collect any proteins bound to the filter membrane on the retentate side, the filter was back flushed with 100 mL GuHCl.

Experiment 4

Removal of GuHCl

Because GuHCl is cytotoxic, removal of GuHCl from the osteoinductive proteins is an important aspect of the present invention. This may be accomplished in the same TFF apparatus as the low molecular weight filtration step by performing one, and more preferably two, diafiltration steps to the low molecular weight filtration retentate. In the present Experiment, the GuHCl concentration was reduced by diafiltration in the LMWU apparatus by slowly adding five retentate volumes (about 0.5 liter) of 1.0 M GuHCl.

To ensure that no osteoinductive proteins were lost, the system was flushed with an additional two retentate volumes (100 ml) of 1.0 M GuHCl to provide a final retentate of about 150 ml of GuHCl containing the dissolved osteoinductive proteins.

Experiment 5

Further Purification by Lyophilization and Precipitation

The diafiltered proteins recovered in GuHCl were frozen and lyophilized to remove water, thereby providing a solid product. The proteins were further purified to ensure complete removal of GuHCl by precipitation in 200 proof ethanol. The ethanol was used to precipitate the proteins while keeping the GuHCl in solution. Fifteen volumes of cold, 200 proof ethanol were added to the protein solution and the mixture was maintained for thirty minutes with constant agitation at 120 rpm at −4° C. to precipitate the proteins and solubilize the GuHCl. The mixture was then centrifuged at 15,000 rpm for twenty minutes. The supernatant was decanted, and the precipitated proteins were rewashed with 200 proof ethanol until all GuHCl was removed. The clean protein precipitate was resolubilized in 10 mM HCl, and either stored solubilized at 4° C. or stored as a solid following lyophilization.

It will be appreciated that alternate means of final purification may be performed. In particular, it may be simpler and easier to conduct multiple diafiltrations to remove GuHCl and urea, or perform a more extensive second diafiltration using greater volumes (e.g., up to several hundred column volumes) of 10 mM HCl. All such embodiments are within the scope of the invention.

Experiment 6

Recovery of Proteins from Acid Demineralization Supernatant

In addition to the recovery of proteins from the DBM itself, BMPs may be recovered from the mineral-containing acid supernatant collected during the bone demineralization step. The mineralized supernatant comprises calcium and phosphate ions in solution with HCl, as well as the desired bone proteins. In the present Experiment, the recovery was performed by first removing at least a portion of the calcium ions by adding about 2.4 liters of 0.72M solution of sodium oxalate to the acid supernatant, precipitating calcium oxalate and buffering the pH of the acid supernatant to about 2.0. The precipitated calcium oxalate was removed by centrifugation (3000 rpm for 15 minutes). PBS (1× concentration) was then added to the solution in an amount sufficient to buffer the pH to 7.0. For about 500 ml of acid supernatant, about 800 ml of PBS was sufficient. The supernatant solution from which calcium has been removed is generally termed a protein supernatant solution.

Isolation of the BMPs from the buffered protein supernatant solution was then achieved by essentially the same processing steps as recited for the DBM itself, i.e., high and low molecular weight ultrafiltration, and additional purification steps. Specifically, a HMWU step in a TFF apparatus was first performed to remove large collagen molecules and fragments from the bone demineralization step. The solution was filtered until the retentate volume was reduced from about 3700 ml to 50 ml. The desired proteins were suspended in the permeate. To ensure that as much protein as possible passed into the permeate, 60 retentate volumes (about 3 liters) of GuHCl was gradually added to the TFF apparatus while maintaining constant retentate volume.

The permeate from the HMWU step was then subjected to a LMWU step substantially as already described in Experiment 3 for the demineralized bone fraction, and further purified as described in Experiments 4 and 5. To avoid duplicative processing, in some instances the buffer/acid supernatant permeate could be combined with the permeate from the demineralized bone fraction and the two fractions could be processed together for the LMWU step, diafiltration into urea and dilute HCl, recovery, lyophilization, acetone precipitation and acid resuspension and lyophilization.

While various embodiments of the present invention have been described in detail, it is apparent that modifications and adaptations of those embodiments will occur to those skilled in the art. For example, the osteoinductive factors can be used in various applications such as treating periodontal diseases and in facial reconstruction, as well as in treating other bone and joint problems. However, it is to be expressly understood that such modifications and adaptations are within the spirit and scope of the present invention, as set forth in the following claims.

What is claimed is:

1. A process for obtaining osteoinductive proteins from mammalian bone tissue, comprising: contacting bone tissue with an acidic demineralization medium to provide demineralized bone tissue and a mineralized supernatant solution; separating the mineralized supernatant solution from the demineralized bone tissue; and removing at least some mineral from the mineralized supernatant solution by performing tangential flow filtration on the mineralized supernatant solution, to yield a demineralized supernatant solution containing osteoinductive proteins.

2. The process of claim 1, wherein the removing step removes essentially all mineral from the mineralized supernatant solution.

3. The process of claim 1, further comprising dialyzing the demineralized supernatant solution to yield a dialyzed supernatant solution.

4. The process of claim 3, further comprising lyophilizing the dialyzed supernatant solution to yield a lyophilized supernatant solution.

5. The process of claim 1, further comprising: extracting osteoinductive proteins from the demineralized supernatant solution; and extracting osteoinductive proteins from the demineralized bone tissue.

6. The process of claim 5, wherein each extracting step comprises contacting the demineralized supernatant solution or the demineralized bone tissue with guanidine hydrochloride (GuHCl).

7. The process of claim 5, further comprising: contacting the demineralized bone tissue with water prior to the extracting steps, to yield wash water and demineralized bone tissue; and extracting osteoinductive proteins from the wash water.

8. A process for obtaining osteoinductive proteins from mammalian bone tissue, comprising: contacting bone tissue with an acidic demineralization medium to provide demineralized bone tissue and a mineralized supernatant solution; separating the mineralized supernatant solution from the demineralized bone tissue; and removing at least some mineral from the mineralized supernatant solution by contacting the mineralized supernatant solution with a mineral precipitation agent, to yield a demineralized supernatant solution containing osteoinductive proteins.

9. The process of claim 8, further comprising: performing tangential flow filtration on the demineralized supernatant solution.

10. The process of claim 8, further comprising: combining the demineralized supernatant solution with the demineralized bone tissue, to yield combined demineralized supernatant solution and demineralized bone tissue; and extracting osteoinductive proteins from the combined demineralized supernatant solution and demineralized bone tissue.

11. The process of claim 8, further comprising: extracting osteoinductive proteins from the demineralized supernatant solution; and extracting osteoinductive proteins from the demineralized bone tissue.

12. The process of claim 9, further comprising: extracting osteoinductive proteins from the demineralized supernatant solution; and extracting osteoinductive proteins from the demineralized bone tissue.

13. The process of claim 10, further comprising: contacting the demineralized bone tissue with water prior to the combining step, to yield wash water and demineralized bone tissue; and extracting osteoinductive proteins from the wash water.

14. The process of claim 11, further comprising: contacting the demineralized bone tissue with water prior to the extracting steps, to yield wash water and demineralized bone tissue; and extracting osteoinductive proteins from the wash water.

15. The process of claim 8, further comprising: extracting osteoinductive proteins from the demineralized supernatant solution.

16. The process of claim 9, further comprising: extracting osteoinductive proteins from the demineralized supernatant solution.

* * * * *

UNITED STATES PATENT AND TRADEMARK OFFICE
CERTIFICATE OF CORRECTION

PATENT NO.       : 7,622,562 B2                                               Page 1 of 1
APPLICATION NO. : 11/553640
DATED            : November 24, 2009
INVENTOR(S)      : Thorne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 422 days.

Signed and Sealed this

Twenty-sixth Day of October, 2010

David J. Kappos
*Director of the United States Patent and Trademark Office*